(12) United States Patent
Cohen

(10) Patent No.: US 6,495,572 B1
(45) Date of Patent: Dec. 17, 2002

(54) SYNERGISTIC MIXTURES OF AN AMINO ACID

(75) Inventor: Yigal Cohen, Kiryat Ono (IL)

(73) Assignee: Agrogene Ltd., Kiryat Ono (IL)

(*) Notice: Subject to any disclaimer, the term of this patent is extended or adjusted under 35 U.S.C. 154(b) by 0 days.

(21) Appl. No.: 09/402,346

(22) PCT Filed: Mar. 30, 1998

(86) PCT No.: PCT/IL98/00151
§ 371 (c)(1),
(2), (4) Date: Jan. 3, 2000

(87) PCT Pub. No.: WO98/44795
PCT Pub. Date: Oct. 15, 1998

(30) Foreign Application Priority Data

| Apr. 4, 1997 | (IL) | ................................................. 120604 |
| Mar. 18, 1998 | (IL) | ................................................. 123722 |

(51) Int. Cl.⁷ ........................ A01N 37/00; A01N 43/40; A01N 43/64

(52) U.S. Cl. ........................ 514/339; 514/557; 514/383; 514/558

(58) Field of Search ................................. 514/557, 558, 514/339, 383

(56) References Cited

U.S. PATENT DOCUMENTS

| 4,894,375 A | * | 1/1990 | Gadebusch et al. | ......... 514/249 |
| 5,814,669 A | * | 9/1998 | Stelzer et al. | ................ 514/626 |
| 5,830,919 A | * | 11/1998 | Cohen | ........................ 514/461 |

FOREIGN PATENT DOCUMENTS

| WO | 96/22690 | * | 8/1996 |

OTHER PUBLICATIONS

Ulrich Gisi (Phytopathology, vol. 86, No. 11, (1996), pp. 1273–1279.*

* cited by examiner

*Primary Examiner*—Sabiha Qazi
(74) *Attorney, Agent, or Firm*—Browdy and Neimark, P.L.L.C.

(57) ABSTRACT

Fungicidal compositions comprising a mixture of β-amino butyric acid and conazoles provide synergistic effects for protecting seeds, plants, and other vegetative material from fungi.

12 Claims, No Drawings

SYNERGISTIC MIXTURES OF AN AMINO ACID

CROSS REFERENCE TO RELATED APPLICATION

The present application is the national stage under 35 U.S.C. 371 of PCT/IL98/00151, filed Mar. 30, 1998.

BACKGROUND OF THE INVENTION

The present invention relates to compositions with useful fungicidal properties. The present invention more particularly relates to synergistic mixtures of fungicides.

β-Aminobutyric acid is reported in copending Israel Patent Applications No. 111,824 as protecting crops against fungal diseases caused by fungi by inducing systemic resistance of said crop.

Conazoles are imidazole or 1,2,4,-triazole compounds containing a halogenated phenyl group having fungicidal properties as described in "Pesticide Manual, Tenth Edition, 1996, published by the British Crop protection council.

OBJECTIVES OF THE INVENTION

It is the objective of the present invention to provide a new fungicidal composition. It is a further objective of the present invention to provide for improved fungicidal compositions which have advantageous properties over the individual components and that often demonstrate synergism and affords a increase in the yield of the crop.

SUMMARY OF THE INVENTION

The present invention provides a fungicidal composition comprising:

(a) β-aminobutyric acid, and (b) a conazole compound which is a steroid demethylation inhibitor.

DETAILED DESCRIPTION OF THE INVENTION

Conazoles are defined in ISO standard 257 as compounds based on imadazole or 1,2,4,-triazole and containing a halogenated phenyl group. Examples include prochloraz, propiconazole, flusilazole, hexaconazole, tebuconazole, difenoconazole, bromuconazole, cyproconazole, diniconazole, fenbuconazole, imibenconazole, furconazole, tetraconazole, myclobutanil, penconazole, fluquinconazole, azaconazole, imazalil, triflumizole, epoxiconazole, triticonazole, metconazole, flutriafol, triadimenol, and the fungicide having the code No. SSF 109 (and their metal complexes-especially complexes with manganese, copper, or zinc).

The names quoted for these conazole compounds are the non-proprietary common names and the chemical structure can be found for example by reference to the "Pesticide Manual", Tenth Edition 1996, published by the British Crop Protection council.

The weight ratio of component (a) to component (b) can vary over wide ranges. Suitable ranges of (a) to (b) are from 800:1 to 1:800 especially 200:1 to 1:200 and most especially 50:1 to 1:50.

In addition other pesticides may be employed in conjunction with the active ingredients described above providing they do not adversely effect the interaction between the fungicidal components.

The composition of the invention are active against a wide range of fungi, e.g. powdery mildew (Erysiphe graminis) on cucumbers and cereal crops such as wheat, barley, oats and rye and other foliar diseases such a glume blotch (Septoria nodorum), leaf blotch (Rhynchosprium secalis), eyespot (Pseudocerocosporella herpotrichoides) and rusts (e.g. Puccinia graminis). Certain compositions of the present invention can be used to control seed-borne organisms such as bunt (Tilletia caries) on wheat, loose smut (Ustilago nuda and Ustilago hordei) on barley and oats, leaf spot (Pyrenophora avenae) on oats and leaf stripe (Pyrenophora graminis) on barley.

The compositions can also be applied to rice for control of rice blast (Pyricularia oryzae), to horticultural crops such as apple trees for the control of apple scab (Venturia inaequalis), roses and other ornamentals for the control of powdery mildew (Sphaerotheca pannosa), rust and black spot, to many crops, for the control of Botrytis cinera, to turf for the control of dollar spot (Sclerotinia homeocarpa) and to stored produce for the control of storage rot organisms of citrus fruit, potatoes, sugar beet, apples, pears etc., (e.g. Penicillium spp., Aspergillus spp. and botrytis spp.). Other diseases that may be combated include Helminthosporium spp. and Cercospora spp.

The composition of the invention may be employed in many forms and are often most conveniently prepared in aqueous form immediately prior to use. One method of preparing such a composition is referred to as "tank mixing" in which the ingredients in their commercially available form are mixed together by the user in a quantity of water. In addition to tank mixing immediately prior to use, the compositions may be formulated into a more concentrated primary composition which is diluted with water or other diluent before use. Such compositions may comprise a surface active agent in addition to the active ingredients and examples of such compositions are as follows.

It can be a dispersible solution which comprises the active ingredients dissolved in a water-miscible solvent with the addition of a dispersing agent. Alternatively it can comprise the ingredients in the form of a finely ground powder in association with a dispersing agent and intimately mixed with water to give a paste or cream which can if desired be added to an emulsion of oil in water to give a dispersion of active ingredients in an aqueous oil emulsion.

An emulsifiable concentrate comprises the active ingredient dissolved in a water-immiscible solvent which is formed into an emulsion with water in the presence of an emulsifying agent.

A granular solid comprises the active ingredients associated with powder diluents such as kaolin, which mixture is granulated by known method. Alternatively it comprises the active ingredients absorbed or absorbed on a pre-granular diluent, for example Fuller's earth, attapulgite or limestone grit.

A dispersible or wettable powder usually comprises the active ingredients in admixture with a suitable surfactant and an inert powder diluent such as china clay.

Another suitable concentrate is a flowable suspension concentrate which is formed by grinding the active ingredients with water, a wetting agent and a suspending agent.

In some circumstances may be desirable to combine two types of formulation e.g. one of the components is present in an emulsifiable concentrate and the second component is dispersed as a powder in this concentrate.

The concentrate of the active ingredients (when used as the sole active components) in a composition for direct application to the crop by conventional ground methods is preferably within the range of 0.001 to 10 percent by weight of the composition, especially 0.005 to 5 percent by weight, but more concentrated compositions containing up to 40 percent may be desirable in the case of aerial sprays.

The compositions of the invention are particularly useful for treating seeds, especially cereal seeds, in order to control, particularly, seed borne diseases. The seeds can be treated in conventional manner using a variety of formulation types, such as dusts, solutions in an organic solvent or aqueous formulations such as flowable suspension concentrates. If cereal grain is to be stored in the store room or container it is sometimes convenient to treat the store room or containers with a composition according to the invention instead of, or in addition to, treatment of the cereal grain itself. A suitable rate of application for a seed dressing is from 0.005 to 5.0 per kilogram of seed, such as for example from 0.01 to 1.0 g per kilogram of seed.

Alternatively the composition of the invention can be applied directly to plants by, for example, spraying or dusting either at the time which the fungus has begun to appear in the plant or before the appearance of fungus, as a protective measure. In both cases the preferred mode of application is by foliar spray. When the composition of the invention is applied directly to the plant a suitable rate of application is from 0.005 to 2 Kilograms per hectare, preferably form 0.1 to 1 Kilogram per hectare.

The invention thus includes a method of combating phytopathogenic fungi which comprises applying to the fungus or its locus a mixture according to the invention.

The invention is illustrated in the following Examples which describe in vivo experiments of potted plants in growth chambers in which a synergistic effect was observed.

EXAMPLE

β Amionbutyric acid and component (b) fungicides were tested against fungi on potted plants, as follows:

12–15 seeds were sown in a pot of 0.5 liter in a mixture of ground, sand, and Perlite in a ratio of 1;1;1. After two weeks in a growth chamber the plants were used for experimentation only when the first true leave appeared. Spraying was done until runoff; waiting in the growth chamber for 24 hours. Inoculations of the fungus was done via dusting the plants with plants already infected. The then dusted plants were incubated 7 to 10 days at 20° in a growth chamber with an exposure of 12 hours to light at an intensity of 7000–800 lucs. The results of the fungul growth was done via visual estimation (0 to 4) of the infected leaves. The existence of synergism between the active components was calculated according to the Abbott Equation.

$$\%\text{ control Expected} = a + b\frac{(ab)}{100}$$

Where a=% control b the β-arninobutyric acid.

b=% control by the second component.

and where the synergism factor. SF is calculated thusly $$SF = \frac{\%\text{ control, observed}}{\%\text{ control, expected}}$$

The efficacy of β-aminobutyric acid and prochloraz in controlling powdery mildew in barley is shown in Table 1. The efficacy of this mixture in controlling powdery mildew in wheat is shown in Table 2. The efficacy of β-aminobutyric acid an propiconazole in controlling powdery mildew in barley is shown in Table 3. The efficacy of this mixture in controlling powdery mildew in wheat is shown in Table 4.

Tables 5–7 show the efficacy of the mixtures of β-aminobutyric acid with tebuconazole, epoxiconazole and triadimenol respectively, in controlling powdery mildew in wheat.

Tables 8–10 show the efficacy of the mixtures of β-aminobutyric acid with tebuconazole, epoxiconazole and triadimenol respectively, in controlling powdery mildew in cucumber.

TABLE1

EFFICACY OF β-AMINOBUTYRIC ACID AND PROCHLORAZ IN CONTROLLING POWDERY MILDEW IN BARLEY

| Concentration of β-Aminobutyric acid (ppm) | concentration of Prochloraz (ppm) | Observed Control (%) | SF |
|---|---|---|---|
| 0 | 1.25 | 43 | — |
| 0 | 5 | 67 | — |
| 0 | 10 | 74 | — |
| 125 | 0 | 14 | — |
| 250 | 0 | 14 | — |
| 500 | 0 | 14 | — |
| 1000 | 0 | 14 | — |
| 125 | 1.25 | 96 | 1.88 |
| 250 | 1.25 | 93 | 1.82 |
| 500 | 1.25 | 84 | 1.65 |
| 1000 | 1.25 | 91 | 1.78 |
| 125 | 5- | 97 | 1.53 |
| 250 | 5- | 94 | — |
| 500 | 5- | 91 | — |
| 1000 | 5- | 83 | — |
| 125 | 10- | 71 | 0.91 |
| 250 | 10- | 89 | 1.14 |
| 500 | 10- | 79 | 1.01 |
| 1000 | 10- | 86 | 1.10 |

TABLE 2

EFFICACY OF β-AMINOBUTYRIC ACID AND PROCHLORAZ IN CONTROLLING POWDERY MILDEW IN WHEAT

| Concentration of β-Aminobutyric acid (ppm) | Concentration of Prochloraz (ppm) | Observed Control (%) | SF |
|---|---|---|---|
| 0 | 1.25 | 33 | — |
| 0 | 5 | 42 | — |
| 0 | 10 | 52 | — |
| 125 | 0 | 8 | — |
| 250 | 0 | 8 | — |
| 500 | 0 | 8 | — |
| 1000 | 0 | 17 | — |
| 125 | 1.25 | 90 | 2.37 |
| 250 | 1.25 | 97 | 2.55 |
| 500 | 1.25 | 72 | 1.89 |
| 1000 | 1.25 | 67 | 1.76 |
| 125 | 5 | 95 | 2.50 |
| 250 | 5 | 97 | 2.50 |
| 500 | 5 | 97 | 2.50 |
| 1000 | 5 | 93 | 2.50 |

TABLE 2-continued

EFFICACY OF β-AMINOBUTYRIC ACID AND PROCHLORAZ IN CONTROLLING POWDERY MILDEW IN WHEAT

| Concentration of β-Aminobutyric acid (ppm) | Concentration of Prochloraz (ppm) | Observed Control (%) | SF |
|---|---|---|---|
| 125 | 10 | 88 | 2.32 |
| 250 | 10 | 95 | 2.50 |
| 500 | 10 | 83 | 2.18 |
| 1000 | 10 | 90 | 2.37 |

TABLE 3

EFFICACY OF β-AMINOBUTYRIC ACID AND PROPICONAZOLE IN CONTROLLING POWDERY MILDEW IN BARLEY

| Concentration of β-Aminobutyric acid (ppm) | Concentration of Propiconazole (ppm) | Observed Control (%) | SF |
|---|---|---|---|
| 0 | 0.5 | 75 | — |
| 0 | 1 | 88 | — |
| 0 | 2 | 94 | — |
| 16 | 0 | 0 | — |
| 62 | 0 | 50 | — |
| 250 | 0 | 38 | — |
| 1000 | 0 | 70 | — |
| 16 | 0.5 | 85 | 1.13 |
| 62 | 0.5 | 95 | 1.09 |
| 250 | 0.5 | 85 | 1.01 |
| 1000 | 0.5 | 80 | 0.86 |
| 16 | 1 | 90 | 1.01 |
| 62 | 1 | 90 | 0.96 |
| 250 | 1 | 88 | 0.95 |
| 1000 | 1 | 91 | 0.99 |
| 16 | 2 | 80 | 0.81 |
| 62 | 2 | 99 | 1.0 |
| 250 | 2 | 96 | 0.97 |
| 1000 | 2 | 98 | 0.99 |

TABLE 4

EFFICACY OF β-AMINOBUTYRIC ACID AND PROPICONAZOLE IN CONTROLLING POWDERY MILDEW IN WHEAT

| Concentration of β-Aminobutyric acid (ppm) | Concentration of Propiconazole (ppm) | Observed Control (%) | SF |
|---|---|---|---|
| 0 | 0.5 | 25 | — |
| 0 | 1 | 50 | — |
| 0 | 2 | 83 | — |
| 16 | 0 | 0 | — |
| 62 | 0 | 8 | — |
| 250 | 0 | 17 | — |
| 1000 | 0 | 33 | — |
| 16 | 0.5 | 58 | 2.32 |
| 62 | 0.5 | 82 | 2.82 |
| 250 | 0.5 | 87 | 2.28 |
| 1000 | 0.5 | 87 | 1.74 |
| 16 | 1 | 63 | 1.26 |
| 62 | 1 | 67 | — |
| 250 | 1 | 90 | — |
| 1000 | 1 | 87 | — |
| 16 | 2 | 98 | 1.18 |
| 62 | 2 | 98 | 1.17 |
| 250 | 2 | 100 | 1.16 |
| 1000 | 2 | 98 | 1.10 |

TABLE 5

SYNERGY BETWEEN β-AMINO BUTYRIC ACID (BABA) AND TEBUCONAZOLE AGAINST POWDERY MILDEW IN WHEET

| Concentration of BABA (ppm) | Concentration of Tebuconazole (ppm) | Observed Control (%) | $ED_{90}$ |
|---|---|---|---|
| 0 | 0.15 | 25 | 1.0 |
| 0 | 0.6 | 63 | 1.0 |
| 0 | 2.5 | 100 | 1.0 |
| 0 | 10 | 100 | 1.0 |
| 125 | 0 | 13 | 684 |
| 250 | 0 | 25 | 684 |
| 500 | 0 | 63 | 684 |
| 1000 | 0 | 100 | 684 |

| | Active Material (ppm) | Observed Control | $ED_{90}$ | Synergy Factor |
|---|---|---|---|---|
| Mixture 20:1 BABA:Tebuconazole | 3.1 | 13 | 13 | 1.5 |
| Mixture 20:1 BABA:Tebuconazole | 12.5 | 88 | 13 | 1.5 |
| Mixture 20:1 BABA:Tebuconazole | 50 | 0 | 13 | 1.5 |
| Mixture 20:1 BABA:Tebuconazole | 200 | 0 | 13 | 1.5 |

TABLE 6

SYNERGY BETWEEN β-AMINO BUTYRIC ACID (BABA) AND EPOXICONAZOLE AGAINST POWDERY MILDEW IN WHEET

| Concentration of BABA (ppm) | Concentration of Epoxiconazole (ppm) | Observed Control (%) | $ED_{90}$ |
|---|---|---|---|
| 0 | 0.15 | 25 | 0.5 |
| 0 | 0.6 | 98 | 0.5 |
| 0 | 2.5 | 100 | 0.5 |
| 0 | 10 | 100 | 0.5 |
| 125 | 0 | 13 | 684 |
| 250 | 0 | 25 | 684 |
| 500 | 0 | 63 | 684 |
| 1000 | 0 | 100 | 684 |

| | Active Material (ppm) | Observed Control | $ED_{90}$ | Synergy Factor |
|---|---|---|---|---|
| Mixture (20:1) BABA:Epoxiconazole | 3.1 | 75 | 6 | 1.6 |
| Mixture (20:1) BABA:Epoxiconazole | 12.5 | 98 | 6 | 1.6 |
| Mixture (20:1) BABA:Epoxiconazole | 50 | 100 | 6 | 1.6 |
| Mixture (20:1) BABA:Epoxiconazole | 200 | 100 | 6 | 1.6 |

TABLE 7

SYNERGY BETWEEN β-AMINO BUTYRIC ACID (BABA) AND TRIADIMENOL AGAINST POWDERY MILDEW IN WHEAT

| Concentration of BABA (ppm) | Concentration of Triadimenol (ppm) | Observed Control (%) | $ED_{90}$ |
|---|---|---|---|
| 0 | 0.15 | 25 | 1.0 |
| 0 | 0.6 | 98 | 1.0 |
| 0 | 2.5 | 100 | 1.0 |
| 0 | 10 | 100 | 1.0 |
| 125 | 0 | 13 | 684 |
| 250 | 0 | 25 | 684 |
| 500 | 0 | 63 | 684 |
| 1000 | 0 | 100 | 684 |

TABLE 7-continued

SYNERGY BETWEEN β-AMINO BUTYRIC ACID (BABA) AND TRIADIMENOL AGAINST POWDERY MILDEW IN WHEET

|  | Active Material (ppm) | Observed Control | $ED_{90}$ | Synergy Factor |
|---|---|---|---|---|
| Mixture 20:1 BABA:Triadimenol | 3.1 | 88 | 5 | 2 |
| Mixture 20:1 BABA:Triadimenol | 12.5 | 98 | 5 | 2 |
| Mixture 20:1 BABA:Triadimenol | 50 | 100 | 5 | 2 |
| Mixture 20:1 BABA:Triadimenol | 200 | 100 | 5 | 2 |

TABLE 8

SYNERGY BETWEEN β-AMINO BUTYRIC ACID (BABA) AND TEBUCONAZOLE AGAINST POWDERY MILDEW IN CUCUMBER

| Concentration of BABA (ppm) | Concentration of Tebuconazole (ppm) | Observed Control (%) | $ED_{90}$ |
|---|---|---|---|
| 0 | 2.5 | 0 | 14 |
| 0 | 5 | 80 | 14 |
| 0 | 10 | 80 | 14 |
| 0 | 20 | 92 | 14 |

|  | Active Material (ppm) | Observed Control | $ED_{90}$ | Synergy Factor |
|---|---|---|---|---|
| Mixture 20:1 BABA:Tebuconazole | 31 | 20 | 84 | 2.6 |
| Mixture 20:1 BABA:Tebuconazole | 62 | 60 | 84 | 2.6 |
| Mixture 20:1 BABA:Tebuconazole | 125 | 100 | 84 | 2.6 |
| Mixture 20:1 BABA:Tebuconazole | 250 | 100 | 84 | 2.6 |

TABLE 9

SYNERGY BETWEEN β-AMINO BUTYRIC ACID (BABA) AND EPOXICONAZOLE AGAINST POWDERY MILDEW IN CUCUMBER

| Concentration of BABA (ppm) | Concentration of Epoxiconazole (ppm) | Observed Control (%) | $ED_{90}$ |
|---|---|---|---|
| 0 | 2.5 | 60 | 5.5 |
| 0 | 5 | 96 | 5.5 |
| 0 | 10 | 96 | 5.5 |
| 0 | 20 | 100 | 5.5 |

|  | Active Material (ppm) | Observed Control | $ED_{90}$ | Synergy Factor |
|---|---|---|---|---|
| Mixture 20:1 BABA:Epoxiconazole | 31 | 96 | 112 | 1.2 |
| Mixture 20:1 BABA:Epoxiconazole | 62 | 96 | 112 | 1.2 |
| Mixture 20:1 BABA:Epoxiconazole | 125 | 96 | 112 | 1.2 |
| Mixture 20:1 BABA:Epoxiconazole | 250 | 96 | 112 | 1.2 |

TABLE 10

SYNERGY BETWEEN β-AMINO BUTYRIC ACID (BABA) AND TRIADIMENOL AGAINST POWDERY MILDEW IN CUCUMBER

| Concentration of BABA (ppm) | Concentration of Triadimenol (ppm) | Observed Control (%) | $ED_{90}$ |
|---|---|---|---|
| 0 | 2.5 | 60 | 9.4 |
| 0 | 5 | 88 | 9.4 |
| 0 | 10 | 96 | 9.4 |
| 0 | 20 | 96 | 9.4 |

|  | Active Material (ppm) | Observed Control | $ED_{90}$ | Synergy Factor |
|---|---|---|---|---|
| Mixture 20:1 BABA:Triadimenol | 31 | 90 | 33 | 4.8 |
| Mixture 20:1 BABA:Triadimenol | 62 | 100 | 33 | 4.8 |
| Mixture 20:1 BABA:Triadimenol | 125 | 100 | 33 | 4.8 |
| Mixture 20:1 BABA:Triadimenol | 250 | 100 | 33 | 4.8 |

What is claimed is:

1. A fungicidal composition comprising a synergistic amount of
   (a) β-aminobutyric acid
   (b) a conazole compound which is a steroid demethylation inhibitor selected from the group consisting of prochloraz, propiconazole, flusilazole, hexaconazole, tebuconzole, difenoconazole, bromuconazole, cyproconazole, diniconazole, fenbuconazole, imibenconazole, furconazole, tetraconazole, myclobutanil, penconazole, fluquinconazole, azaconazole, imazalil, triflumizole, epoxiconazole, triticonazole, metconazole, flutriafol, triadiminol and their metal complexes with manganese, copper, or zinc wherein the compound ratio of β-aminobutyria acid to the conazoles is in the range of 800:1 to 8:1.

2. A composition in accordance with claim 1 wherein the conazole compound is selected from the group consisting of prochloraz, propiconazole, tebuconazole, epoxiconazole and triadimenol and their metal complexes with manganese, copper and zinc.

3. A method of combatting phytopathogenic fungi which comprises applying to seeds, plants and other vegetative material or their habitat an effective amount of a synergistic combination of
   (a) β-Aminobutyric acid
   (b) a conazole compound which is a steroid demethylation inhibitor, comprising (a) and (b) being applied either together or in sequence, said conazole compound being selected from groups consisting of prochloraz, propiconazole, flusilazole, hexaconazole, tebuconazole, difenoconazole, bromuconazole, cyproconazole, diniconazole, fenbuconazole, imibenconazole, furconazole, tetraconazole, myclobutanil, penconazole, fluquinconazole, azaconazole, imazalil, triflumizole, epoxiconazole, triticonazole, metconazole, flutriafol, triadimenol, and their metal complexes with manganese, copper, or zinc, wherein the proportions of β-aminobutyric acid to conazole compound range from 1:800 to 8:1.

4. A method in accordance with claim 3 the conazole steroid demethylator inhibitor is selected from the group consisting of prochloraz, propiconazole, tebuconazole, epoxiconazole, triadimienol and their metal complexes with manganese, copper or zinc.

5. A method in accordance with claim 3 wherein the crop is cereals and cucumbers.

6. A method in accordance with claim 3 wherein the disease is powdery mildew.

7. A composition according to claim 1 wherein the ratio of β-aminobutyric acid to the conazole is in the range 200:1 to 8:1 based on the weight of the conazole compound.

8. A composition according to claim 1 wherein the ratio of β-aminobutyric acid to the conazole is in the range 50:1 to 8:1 based on the weight of the conazole compound.

9. A method on accordance with claim 4 wherein the crop is cereals and cucumbers.

10. A method in accordance with claim 4 wherein the disease is powdery mildew.

11. A method in accordance with claim 7 wherein the disease is powdery mildew.

12. A method in accordance with claim 8 wherein the disease is powdery mildew.

* * * * *